US008957148B2

(12) United States Patent
Addcox et al.

(10) Patent No.: US 8,957,148 B2
(45) Date of Patent: Feb. 17, 2015

(54) POLYMER COMPOSITIONS HAVING IMPROVED BARRIER PROPERTIES

(71) Applicant: Chevron Phillips Chemical Company LP, The Woodlands, TX (US)

(72) Inventors: Jim H. Addcox, The Woodlands, TX (US); Guylaine St. Jean, Bartlesville, OK (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 24 days.

(21) Appl. No.: 13/753,132

(22) Filed: Jan. 29, 2013

(65) Prior Publication Data
US 2014/0212607 A1   Jul. 31, 2014

(51) Int. Cl.
*C08K 5/01*      (2006.01)
*C08L 23/06*     (2006.01)
*A61F 13/514*    (2006.01)
*C08J 5/18*      (2006.01)
*C08L 23/08*     (2006.01)
*C08L 23/04*     (2006.01)

(52) U.S. Cl.
CPC ........... *C08L 23/06* (2013.01); *A61F 13/51462* (2013.01); *C08J 5/18* (2013.01); *C08L 23/08* (2013.01); *C08L 23/04* (2013.01); *C08L 2203/16* (2013.01)
USPC .......................................... 524/487; 524/587

(58) Field of Classification Search
USPC ....................................................... 524/487
See application file for complete search history.

(56) References Cited

U.S. PATENT DOCUMENTS

| | | | |
|---|---|---|---|
| 3,248,179 A | | 4/1966 | Norwood |
| 4,501,885 A | | 2/1985 | Sherk et al. |
| 4,588,790 A | | 5/1986 | Jenkins, III et al. |
| 5,141,801 A | | 8/1992 | Takeshita et al. |
| 5,155,160 A | * | 10/1992 | Yeh et al. ................. 524/487 |
| 5,352,749 A | | 10/1994 | DeChellis et al. |
| 5,436,304 A | | 7/1995 | Griffin et al. |
| 5,455,314 A | | 10/1995 | Burns et al. |
| 5,565,175 A | | 10/1996 | Hottovy et al. |
| 5,575,979 A | | 11/1996 | Hanson |
| 6,033,771 A | * | 3/2000 | Heffelfinger ............... 428/320.2 |
| 6,239,235 B1 | | 5/2001 | Hottovy et al. |
| 6,262,191 B1 | | 7/2001 | Hottovy et al. |
| 6,312,825 B1 | | 11/2001 | Su et al. |
| 6,528,572 B1 | | 3/2003 | Patel et al. |
| 6,833,415 B2 | | 12/2004 | Kendrick et al. |
| 7,064,225 B2 | | 6/2006 | Thorn et al. |
| 7,222,886 B2 | | 5/2007 | Kim et al. |
| 7,517,939 B2 | | 4/2009 | Yang et al. |
| 8,188,190 B2 | | 5/2012 | Vignola |
| 8,436,085 B2 | | 5/2013 | Borke et al. |
| 2008/0003910 A1 | | 1/2008 | Hughes et al. |
| 2008/0118749 A1 | | 5/2008 | Aubee et al. |
| 2013/0059103 A1 | * | 3/2013 | Yang et al. ................. 428/36.92 |
| 2013/0068134 A1 | * | 3/2013 | Yang et al. ................. 106/270 |

FOREIGN PATENT DOCUMENTS

| | | |
|---|---|---|
| EP | 1152025 | 11/2001 |
| EP | 1152025 A1 | 11/2001 |
| WO | 9903673 A1 | 1/1999 |

OTHER PUBLICATIONS

AlphaPlus material safety data sheet entitled "AlphaPlus® C30+ Sales Specifications," Jul. 2010, 1 page, Chevron Phillips Chemical Company LP.
AlphaPlus material safety data sheet entitled "AlphaPlus® Oxidized C30+ Wax Sales Specifications," Jul. 2010, 1 page, Chevron Phillips Chemical Company LP.
Bird, R. Byron, et al., "Dynamics of polymeric liquids," Fluid Mechanics, 1987, pp. 171-172 plus 8 pages including cover, publishing, and contents information, vol. 1, Second Edition, John Wiley & Sons, Inc.
ChemWatch material safety data sheet entitled "Paraffin," Nov. 14, 2009, pp. 1-12.
"Group notation revised in periodic table," Feb. 4, 1985, pp. 26-27, C&EN.
Hieber, C. A., et al., "Shear-rate-dependence modeling of polymer melt viscosity," Polymer Engineering and Science, Jul. 1992, pp. 931-938, vol. 32, No. 14.
Hieber, C. A., et al., "Some correlations involving the shear viscosity of polystyrene melts," Rheologica Acta, 1989, pp. 321-332, vol. 28, No. 4.
McNaught, Alan D., et al., "Compendium of chemical terminology," International Union of Pure and Applied Chemistry, Second edition, 1997, 1 page cover and publishing information, Wiley-Blackwell.
STRUKTOL brochure entitled "STRUKTOL® Montan Wax OP," Oct. 4, 2000, 1 page.
STRUKTOL technical data sheet entitled "STRUKTOL® TR 016," May 4, 2005, 2 pages, Struktol Company of America.
International Search Report for PCT/US2014/011972 dated Jan. 4, 2014.
Foreign communication from a related counterpart application—International Search Report, PCT/US2014/011972, Apr. 1, 2014, 3 pages.

* cited by examiner

*Primary Examiner* — Hui Chin
(74) *Attorney, Agent, or Firm* — Conley Rose, P.C.; Rodney B. Carroll; Cheryl L. Huseman

(57) ABSTRACT

A composition comprising a polymer and a wax wherein the polymer has a melt index of from about 0.5 g/10 min to about 4 g/10 min, a density of equal to or greater than about 0.945 g/cc which when formed into a film displays a moisture vapor transmission rate of less than about 0.55 g-mil/100 in$^2$ in 24 hours as determined in accordance with ASTM F 1249.

19 Claims, 6 Drawing Sheets

POLYMER COMPOSITIONS HAVING IMPROVED BARRIER PROPERTIES

TECHNICAL FIELD

The present disclosure relates to polymeric compositions, more specifically polyethylene (PE) compositions, and articles made from same.

BACKGROUND

Polyolefins are plastic materials useful for making a wide variety of valued products due to their combination of stiffness, ductility, barrier properties, temperature resistance, optical properties, availability, and low cost. One of the most valued products is plastic films. In particular, PE is the one of the largest volume polymers consumed in the world. It is a versatile polymer that offers high performance relative to other polymers and alternative materials such as glass, metal or paper. Plastic films such as PE films are mostly used in packaging applications but they also find utility in the agricultural, medical, and engineering fields.

PE films are manufactured in a variety of grades that are usually differentiated by the polymer density such that PE films can be designated for example, low density polyethylene (LDPE), linear low density polyethylene (LLDPE), medium density polyethylene (MDPE), and high density polyethylene (HDPE), wherein each density range has a unique combination of properties making it suitable for a particular application.

Despite the many positive attributes of PE, the film product remains permeable to gases such as oxygen or carbon dioxide and/or moisture (e.g., water). Thus, it would be desirable to develop a PE film product exhibiting improved bather properties.

SUMMARY

Disclosed herein is a composition comprising a polymer and a wax wherein the polymer has a melt index of from about 0.5 g/10 min to about 4 g/10 min, a density of equal to or greater than about 0.945 g/cc which when formed into a film displays a moisture vapor transmission rate of less than about 0.55 g-mil/100 in$^2$ in 24 hours as determined in accordance with ASTM F 1249.

Also disclosed herein is a composition comprising a metallocene-catalyzed unimodal polyethylene homopolymer and an oxidized olefin wax wherein the oxidized olefin wax comprises one of more of the following: a) greater than 90 wt % olefins having from 20 to 24 carbon atoms and greater than 75 mol. % alpha olefins having from 20 to 24 carbon atoms; b) greater than 70 wt % olefins having from 24 to 28 carbon atoms and greater than 45 mol. % alpha olefins having from 24 to 28 carbon atoms; c) greater than 90 wt % olefins having from 26 to 28 carbon atoms and greater than 75 mol. % alpha olefins having from 26 to 28 carbon atoms; d) greater than 80 wt % olefins having at least 30 carbon atoms and greater than 45 mol. % alpha olefins having at least 30 carbon atoms; or e) greater than 85 wt % olefins having at least 30 carbon atoms and greater than 75 mol. % alpha olefins at least 30 carbon atoms.

DETAILED DESCRIPTION

Figure 1A:
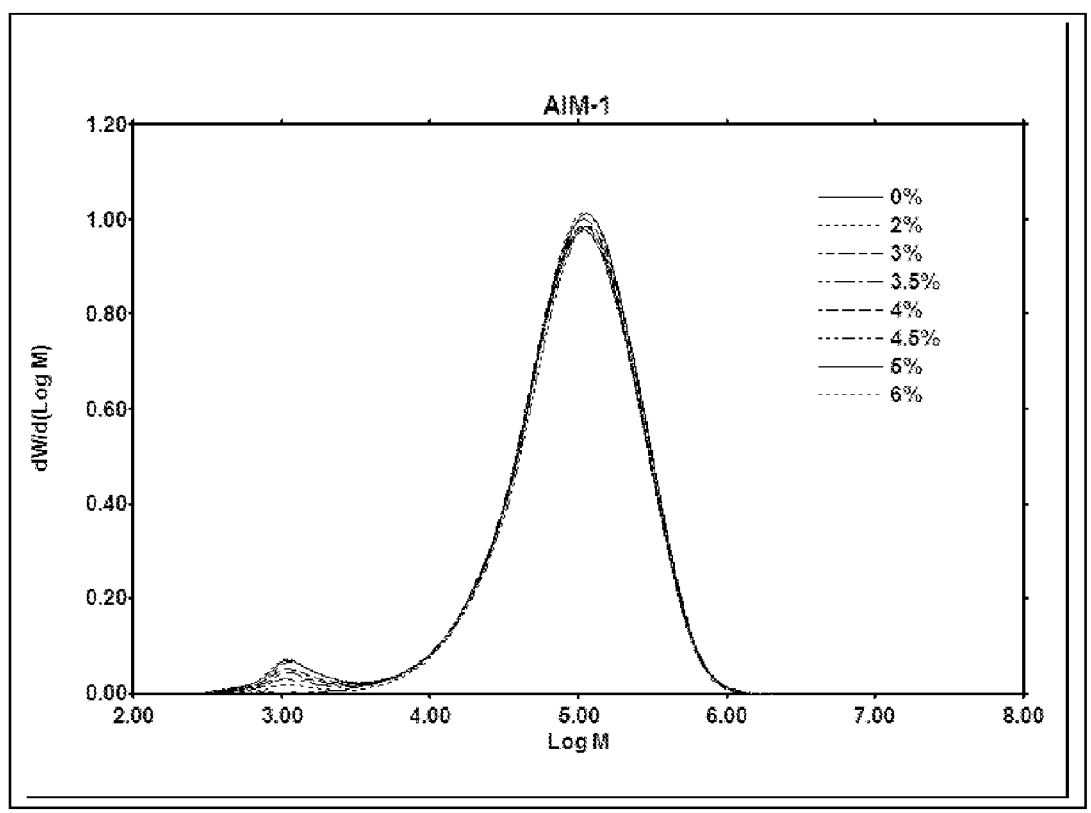
FIGS. 1A-1D are molecular weight distribution profiles for the samples from example 1.
Figure 1B:
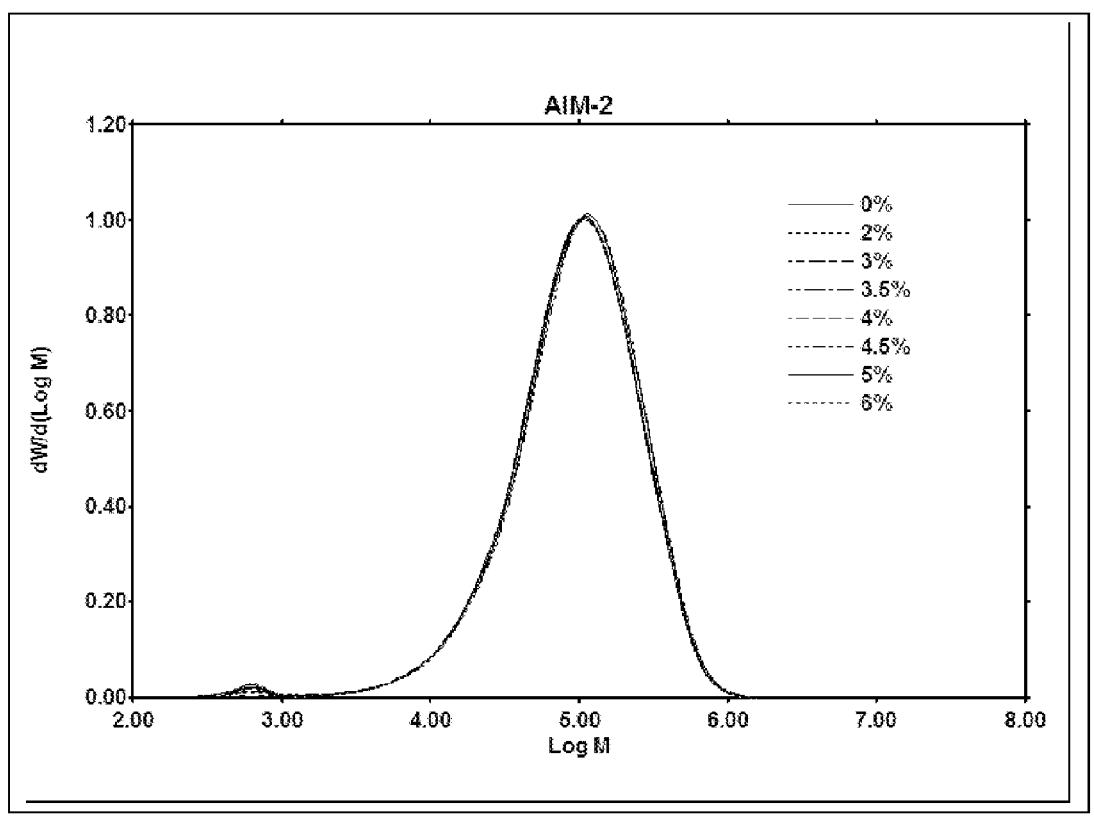
Figure 1C:
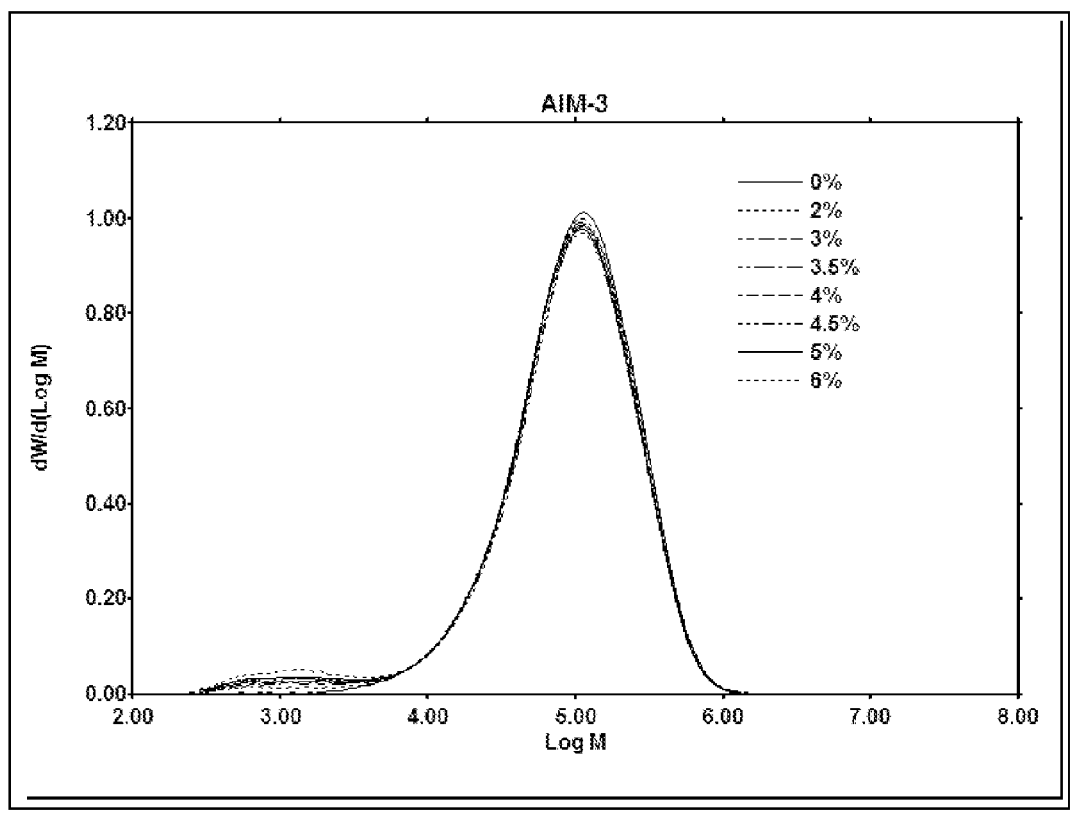
Figure 1D:
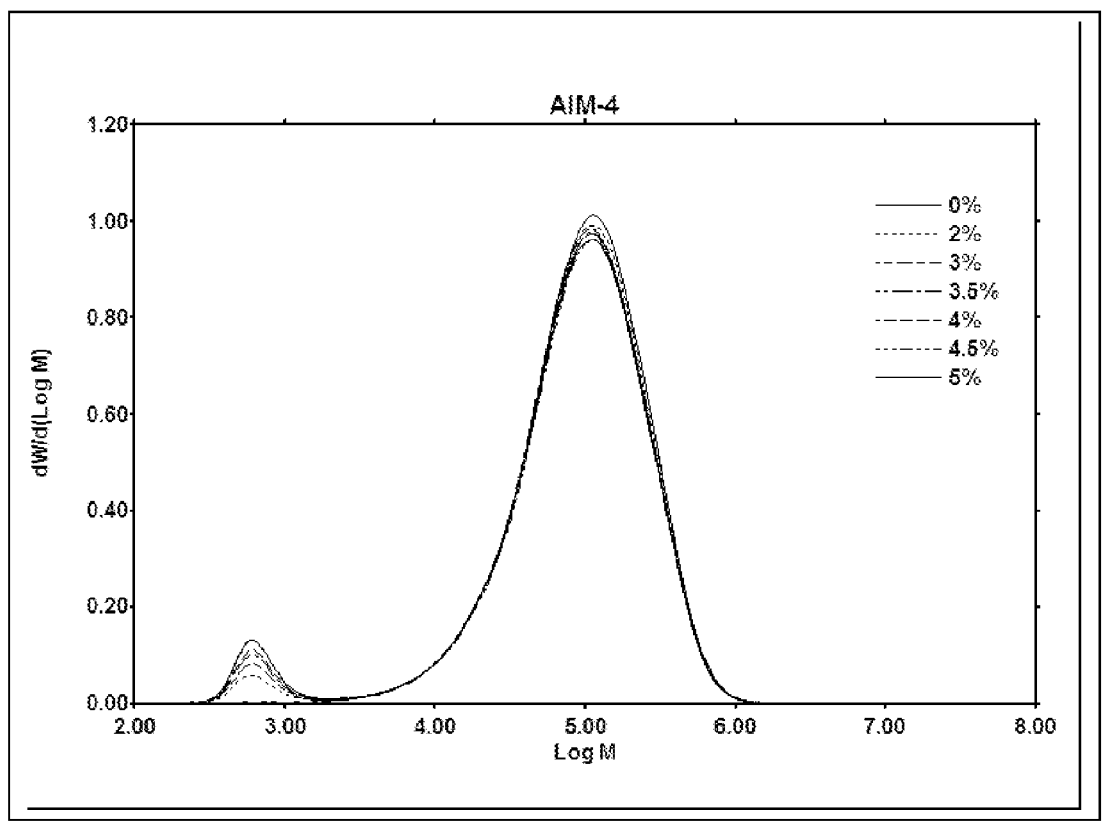

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2$^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the table are indicated using the numbering scheme indicated in the version of the periodic table of elements published in *Chemical and Engineering News*, 63(5), 27, 1985. In some instances, a group of elements can be indicated using a common name assigned to the group; for example alkali earth metals (or alkali metals) for Group 1 elements, alkaline earth metals (or alkaline metals) for Group 2 elements, transition metals for Group 3-12 elements, and halogens for Group 17 elements.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter the composition or method to which the term is applied. For example, a feedstock consisting of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class which is utilized and it is possible to have different transitional terms or phrases utilized with different features within a claim. For example, a method can comprise several recited steps (and other non-recited steps) but utilize a catalyst system preparation consisting of specific or alternatively, consist of specific steps and/or utilize a catalyst system comprising recited components and other non-recited components.

Within this disclosure, use of "comprising" or an equivalent expression contemplates the use of the phrase "consisting essentially of," "consists essentially of," or equivalent expressions as an alternative embodiments to the open-ended expression. Additionally, use of "comprising" or an equivalent expression or use of "consisting essentially of" in the specification contemplates the use of the phrase "consisting of," "consists of," or equivalent expression as an alternative to the open-ended expression or middle ground expression, respectively. For example, "comprising" should be understood to include "consisting essentially of," and "consisting of" as alternative embodiments for the aspect, features, and/or elements presented in the specification unless specifically indicated otherwise.

The terms "a," "an," and "the" are intended, unless specifically indicated otherwise, to include plural alternatives, e.g., at least one. For instance, the disclosure of "a normal alpha olefin" is meant to encompass one normal alpha olefin, or mixtures or combinations of more than one normal alpha olefin unless otherwise specified.

The term "hydrocarbon" whenever used in this specification and claims refers to a compound containing only carbon and hydrogen. A "paraffin" whenever used in this specification and claims refers to a saturated "hydrocarbon."

The term "wax" whenever used in this specification and claims refers to an organic material having a melting point greater than 35° C. at 1 atmosphere. The term "wax composition" whenever used in this specification and claims refers to a composition comprising a wax or wax molecules. The term "wax composition" can refer to a composition comprising, consisting essentially of, or consisting of, a wax or wax molecules. Compounds which are not wax molecules (e.g. solvents and additives, among others) can be present in a "wax composition" comprising a wax. The term "hydrocarbon wax" whenever used in this specification and claims refers to wax molecules which are hydrocarbons; i.e., hydrocarbon wax molecules. The term "hydrocarbon wax composition" whenever used in this specification and claims refers to a composition comprising hydrocarbon wax molecules. Compounds which are not a hydrocarbon wax molecule (e.g., solvents, and/or non-hydrocarbon and/or non-wax impurities, among others) can be present in the "hydrocarbon wax composition" or a "hydrocarbon wax composition comprising a hydrocarbon wax" unless otherwise indicated. Hydrocarbon wax compositions comprising, consisting essentially of, or consisting of, a hydrocarbon wax refer to compositions consistent with the definitions of hydrocarbon wax, comprising, consisting essentially of, and consisting of, as provided herein. The term "olefin wax" whenever used in this specification and claims refers to wax molecules which are olefinic. The term "olefin wax composition" whenever used in this specification and claims refers to a compositions comprising olefin wax molecules. Compounds which are not an olefin wax molecule (e.g., solvents, and/or non-olefin and/or non-wax impurities, among others) can be present in the "olefin wax composition." Olefin wax compositions comprising, consisting essentially of, or consisting of, a hydrocarbon wax refer to compositions consistent with the definitions of olefin wax, comprising, consisting essentially of, and consisting of as provided herein. Other waxes, wax molecules, and/or wax compositions can be readily envisioned using other descriptors or combinations of descriptors and would conform to same use patterns.

The term "olefin" whenever used in this specification and claims refers to compounds that have at least one carbon-carbon double bond that is not part of an aromatic ring or ring system. The term "olefin" includes aliphatic and aromatic, cyclic and cyclic, and/or linear and branched compounds having at least one carbon-carbon double bond that is not part of an aromatic ring or ring system unless specifically stated otherwise. The term "olefin," by itself, does not indicate the presence or absence of heteroatoms and/or the presence or absence of other carbon-carbon double bonds unless explicitly indicated. Olefins having only one, only two, only three, etc. . . . carbon-carbon double bonds can be identified by use of the term "mono," "di," "tri," etc. . . . within the name of the olefin. The olefins can be further identified by the position of the carbon-carbon double bond(s).

The term "alkene" whenever used in this specification and claims refers to a hydrocarbon olefin that has at least one non-aromatic carbon-carbon double bond. The term "alkene" includes aliphatic or aromatic (an alkene having an aromatic substituent within the compound), cyclic or acyclic, and/or linear and branched compounds having at least one non-aromatic carbon-carbon double bond unless expressly stated otherwise. Alkenes having only one, only two, only three, etc. . . . such multiple bond can be identified by use of the term "mono," "di," "tri," etc. . . . within the name. For example, alkamonoenes, alkadienes, and alkatrienes refer to a linear or branched hydrocarbon olefins having only one carbon-carbon double bond (general formula $C_nH_{2n}$), only two carbon-carbon double bonds (general formula $C_nH_{2n-2}$), and only three carbon-carbon double bonds (general formula $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replace with a halogen atom.

The term "alpha olefin" as used in this specification and claims refers to an olefin that has a double bond between the first and second carbon atom of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of heteroatoms and/or the presence or absence of other carbon-carbon double bonds unless explicitly indicated. The terms "hydrocarbon alpha olefin" or "alpha olefin hydrocarbon" refer to alpha olefin compounds containing only hydrogen and carbon.

The term "linear alpha olefin" as used herein refers to a linear olefin having a double bond between the first and second carbon atom. The term "linear alpha olefin" by itself does not indicate the presence or absence of heteroatoms and/or the presence or absence of other carbon-carbon double bonds, unless explicitly indicated. The terms "linear hydrocarbon alpha olefin" or "linear alpha olefin hydrocarbon" refers to linear alpha olefin compounds containing only hydrogen and carbon.

The term "normal alpha olefin" whenever used in this specification and claims refers to a linear hydrocarbon mono-olefin having a double bond between the first and second carbon atom. It is noted that "normal alpha olefin" is not synonymous with "linear alpha olefin" as the term "linear alpha olefin" can include linear olefinic compounds having a double bond between the first and second carbon atoms and having heteroatoms and/or additional double bonds.

Acid number values, when referred to herein, were measured according to ASTM D974-07, unless explicitly stated to the contrary, and refers to the number of milligrams of potassium hydroxide (KOH) required to neutralize one gram material. Saponification numbers, when referred to herein, were measured by ASTM D94-07, unless explicitly stated to the contrary, and refers to the number of milligrams of potassium hydroxide (KOH) required to saponify 1 g of material. Needle penetrations when referred to herein, were measured according to ASTM D1321-86, unless explicitly stated to the contrary. Drop melt points, when referred to herein, were measured according to ASTM D127-87, unless explicitly stated to the contrary. All kinematic viscosities are the 100° C. kinematic viscosities as measured by ASTM D445-96, unless explicitly stated to the contrary. All ASTM standards referred to herein are the most current versions as of the filing date of the present application.

Disclosed herein are polymers, polymeric compositions, polymeric articles, and methods of making same. The polymers and/or polymeric compositions of the present disclosure may comprise a mixture of a base polymer and an additive to form a polymer composition having one or more improved bather properties. Such compositions are designated compositions with improved bather properties (CM).

In an embodiment, the base polymer comprises an olefin polymer, alternatively an ethylene polymer or alternatively an ethylene homopolymer. Herein, the disclosure will refer to the base polymer as a polyethylene polymer (PE). A PE polymer suitable for use in the present disclosure is produced by any olefin polymerization method, using various types of polymerization reactors. As used herein, "polymerization reactor" includes any reactor capable of polymerizing olefin monomers to produce homopolymers and/or copolymers. Homopolymers and/or copolymers produced in the reactor may be referred to as resin and/or polymers. The various types of reactors include, but are not limited to those that may be referred to as batch, slurry, gas-phase, solution, high pressure, tubular, autoclave, or other reactor and/or reactors. Gas phase reactors may comprise fluidized bed reactors or staged horizontal reactors. Slurry reactors may comprise vertical and/or horizontal loops. High pressure reactors may comprise autoclave and/or tubular reactors. Reactor types may include batch and/or continuous processes. Continuous processes may use intermittent and/or continuous product discharge or transfer. Processes may also include partial or full direct recycle of un-reacted monomer, un-reacted comonomer, catalyst and/or co-catalysts, diluents, and/or other materials of the polymerization process.

Polymerization reactor systems of the present disclosure may comprise one type of reactor in a system or multiple reactors of the same or different type, operated in any suitable configuration. Production of polymers in multiple reactors may include several stages in at least two separate polymerization reactors interconnected by a transfer system making it possible to transfer the polymers resulting from the first polymerization reactor into the second reactor. Alternatively, polymerization in multiple reactors may include the transfer, either manual or automatic, of polymer from one reactor to subsequent reactor or reactors for additional polymerization. Alternatively, multi-stage or multi-step polymerization may take place in a single reactor, wherein the conditions are changed such that a different polymerization reaction takes place.

The desired polymerization conditions in one of the reactors may be the same as or different from the operating conditions of any other reactors involved in the overall process of producing the polymer of the present disclosure. Multiple reactor systems may include any combination including, but not limited to multiple loop reactors, multiple gas phase reactors, a combination of loop and gas phase reactors, multiple high pressure reactors or a combination of high pressure with loop and/or gas reactors. The multiple reactors may be operated in series or in parallel. In an embodiment, any arrangement and/or any combination of reactors may be employed to produce the polymer of the present disclosure.

According to one embodiment, the polymerization reactor system may comprise at least one loop slurry reactor. Such reactors are commonplace, and may comprise vertical or horizontal loops. Monomer, diluent, catalyst system, and optionally any comonomer may be continuously fed to a loop slurry reactor, where polymerization occurs. Generally, continuous processes may comprise the continuous introduction of a monomer, a catalyst, and/or a diluent into a polymerization reactor and the continuous removal from this reactor of a suspension comprising polymer particles and the diluent. Reactor effluent may be flashed to remove the liquids that comprise the diluent from the solid polymer, monomer and/or comonomer. Various technologies may be used for this separation step including but not limited to, flashing that may include any combination of heat addition and pressure reduction; separation by cyclonic action in either a cyclone or hydrocyclone; separation by centrifugation; or other appropriate method of separation.

Typical slurry polymerization processes (also known as particle-form processes) are disclosed in U.S. Pat. Nos. 3,248,179, 4,501,885, 5,565,175, 5,575,979, 6,239,235, 6,262,191 and 6,833,415, for example; each of which are herein incorporated by reference in their entirety.

Suitable diluents used in slurry polymerization include, but are not limited to, the monomer being polymerized and hydrocarbons that are liquids under reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used. An example is polymerization of propylene monomer as disclosed in U.S. Pat. No. 5,455,314, which is incorporated by reference herein in its entirety.

According to yet another embodiment, the polymerization reactor may comprise at least one gas phase reactor. Such systems may employ a continuous recycle stream containing one or more monomers continuously cycled through a fluidized bed in the presence of the catalyst under polymerization conditions. A recycle stream may be withdrawn from the fluidized bed and recycled back into the reactor. Simultaneously, polymer product may be withdrawn from the reactor and new or fresh monomer may be added to replace the polymerized monomer. Such gas phase reactors may comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 4,588,790, 5,352,749, and 5,436,304, each of which is incorporated by reference in its entirety herein.

According to still another embodiment, a high pressure polymerization reactor may comprise a tubular reactor or an autoclave reactor. Tubular reactors may have several zones where fresh monomer, initiators, or catalysts are added. Monomer may be entrained in an inert gaseous stream and introduced at one zone of the reactor. Initiators, catalysts, and/or catalyst components may be entrained in a gaseous stream and introduced at another zone of the reactor. The gas streams may be intermixed for polymerization. Heat and pressure may be employed appropriately to obtain optimal polymerization reaction conditions.

According to yet another embodiment, the polymerization reactor may comprise a solution polymerization reactor wherein the monomer is contacted with the catalyst composition by suitable stirring or other means. A carrier comprising an organic diluent or excess monomer may be employed. If desired, the monomer may be brought in the vapor phase into contact with the catalytic reaction product, in the presence or absence of liquid material. The polymerization zone is maintained at temperatures and pressures that will result in the formation of a solution of the polymer in a reaction medium. Agitation may be employed to obtain better temperature control and to maintain uniform polymerization mixtures throughout the polymerization zone. Adequate means are utilized for dissipating the exothermic heat of polymerization.

Polymerization reactors suitable for the present disclosure may further comprise any combination of at least one raw material feed system, at least one feed system for catalyst or catalyst components, and/or at least one polymer recovery system. Suitable reactor systems for the present invention may further comprise systems for feedstock purification, catalyst storage and preparation, extrusion, reactor cooling, polymer recovery, fractionation, recycle, storage, loadout, laboratory analysis, and process control.

Conditions that are controlled for polymerization efficiency and to provide polymer properties include, but are not limited to temperature, pressure, type and quantity of catalyst or co-catalyst, and the concentrations of various reactants. Polymerization temperature can affect catalyst productivity, polymer molecular weight and molecular weight distribution. Suitable polymerization temperatures may be any temperature below the de-polymerization temperature, according to the Gibbs Free Energy Equation. Typically this includes from about 60° C. to about 280° C., for example, and/or from about 70° C. to about 110° C., depending upon the type of polymerization reactor and/or polymerization process.

Suitable pressures will also vary according to the reactor and polymerization process. The pressure for liquid phase polymerization in a loop reactor is typically less than 1000 psig. Pressure for gas phase polymerization is usually at about 200-500 psig. High pressure polymerization in tubular or autoclave reactors is generally run at about 20,000 to 75,000 psig. Polymerization reactors can also be operated in a supercritical region occurring at generally higher temperatures and pressures. Operation above the critical point of a pressure/temperature diagram (supercritical phase) may offer advantages.

The concentration of various reactants can be controlled to produce polymers with certain physical and mechanical properties. The proposed end-use product that will be formed by the polymer and the method of forming that product may be varied to determine the desired final product properties. Mechanical properties include, but are not limited to tensile strength, flexural modulus, impact resistance, creep, stress relaxation and hardness tests. Physical properties include, but are not limited to density, molecular weight, molecular weight distribution, melting temperature, glass transition temperature, temperature melt of crystallization, density, stereoregularity, crack growth, short chain branching, long chain branching and rheological measurements.

The concentrations of monomer, co-monomer, hydrogen, co-catalyst, modifiers, and electron donors are generally important in producing specific polymer properties. Comonomer may be used to control product density. Hydrogen may be used to control product molecular weight. Co-catalysts may be used to alkylate, scavenge poisons and/or control molecular weight. The concentration of poisons may be minimized, as poisons may impact the reactions and/or otherwise affect polymer product properties. Modifiers may be used to control product properties and electron donors may affect stereoregularity.

In an embodiment, a method of preparing a polymer suitable for use in the present disclosure comprises contacting an olefin and/or alpha-olefin monomer with a catalyst system under conditions suitable for the formation of a polymer of the type described herein. In an embodiment, a catalyst composition or system for the production of a polymer of the type disclosed herein may comprise a single metallocene compound; an activator support, and an organoaluminum compound. Herein, the term "metallocene" describes a compound comprising at least one $\eta^3$ to $\eta^5$-cyclo alkadienyl-type moiety, wherein $\eta^3$ to $\eta^5$-cyclo alkadienyl moieties include cyclopentadienyl ligands, indenyl ligands, fluorenyl ligands, and the like, including partially saturated or substituted derivatives or analogs of any of these. Possible substituents on these ligands include hydrogen, therefore the description "substituted derivatives thereof" in this disclosure comprises partially saturated ligands such as tetrahydroindenyl, tetrahydrofluorenyl, octahydrofluorenyl, partially saturated indenyl, partially saturated fluorenyl, substituted partially saturated indenyl, substituted partially saturated fluorenyl, and the like.

In an embodiment, the metallocene comprises a tightly-bridged ansa-metallocene compound comprising an olefin-containing moiety bonded to a cyclopentadienyl-type ligand and at least one aryl group bonded to the bridging atom of the bridging ligand. As used herein, the term bridged or ansa-metallocene refers simply to a metallocene compound in which the two $\eta^5$-cycloalkadienyl-type ligands in the molecule are linked by a bridging moiety. Useful ansa-metallocenes are typically "tightly-bridged," meaning that the two $\eta^5$-cycloalkadienyl-type ligands are connected by a bridging group wherein the shortest link of the bridging moiety between the $\eta^5$-cycloalkadienyl-type ligands is a single atom. Thus, the length of the bridge or the chain between the two $\eta^5$-cycloalkadienyl-type ligands is one atom, although this bridging atom is substituted. The metallocenes of this disclosure are therefore bridged bis($\eta^5$-cycloalkadienyl)-type compounds, wherein the $\eta^5$-cycloalkadienyl portions include substituted cyclopentadienyl ligands, substituted indenyl ligands, substituted fluorenyl ligands, and the like, wherein one substituent on these cyclopentadienyl-type ligands is a bridging group having the formula $ER^1R^2$, wherein E is a carbon atom, a silicon atom, a germanium atom, or a tin atom, and wherein E is bonded to both cyclopentadienyl-type ligands. In this aspect, $R^1$ and $R^2$ can be independently selected from an alkyl group or an aryl group, either of which having up to 12 carbon atoms, or hydrogen. A metallocene compound suitable for use in the present disclosure may display a positive hydrogen response. Herein a positive hydrogen response refers to a lowering of the molecular weight. Examples of metallocene compounds suitable for use in the present disclosure are described in more detail in U.S. Pat. Nos. 7,064,225; 7,222,886 and 7,517,939 each of which is incorporated herein by reference in its entirety.

In an embodiment, an organoaluminum compound suitable for use in the catalyst composition or system comprises an alkylaluminum compound. For example, the organoaluminum compound may comprise a trialkylaluminum compound, having the general formula $AlR_3$. Nonlimiting examples of trialkylaluminum compounds suitable for use in this disclosure include triisobutylaluminum (TiBA or TiBAl); tri-n-butylaluminum (TNBA); tri-octly-butylaluminum (TOBA); triethylaluminum (TEA); and/or other appropriate alkyl-aluminum complexes, and combinations thereof. Additionally, partially hydrolyzed alkylaluminum compounds and/or aluminoxanes, may be used. In an embodiment, the organoaluminum compound comprises a compound represented by the general formula:

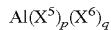

where $X^5$ is a halide, hydrocarbyloxide group, hydrocarbylamino group or combinations thereof; $X^6$ is a hydrocarbyl group having up to 18 carbon atom; p ranges from 0 to 2; and q is 3-p.

In one aspect, the activator-support comprises a chemically-treated solid oxide. Alternatively, the activator-support can comprise a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, or any combination thereof. Examples of catalyst compositions and systems suitable for use in the preparation of polymers of the type disclosed herein can be found in U.S. patent application Ser. No. 13/224,775 which is incorporated by reference herein in its entirety.

The polymer may include other additives. Examples of additives include, but are not limited to, antistatic agents, colorants, stabilizers, nucleators, surface modifiers, pigments, slip agents, antiblocks, tackafiers, polymer processing aids, and combinations thereof. Such additives may be used singularly or in combination and may be included in the polymer before, during, or after preparation of the polymer as described herein. Such additives may be added via any suitable technique, for example during an extrusion or compounding step such as during pelletization or subsequent processing into an end use article.

In an embodiment, ethylene is polymerized using the methodologies disclosed herein to produce a PE base polymer. In an embodiment, the PE base polymer is a homopolymer. It is to be understood that an inconsequential amount of comonomer may be present in the polymers disclosed herein and the polymer still be considered a homopolymer. Herein, an inconsequential amount of a comonomer refers to an amount that does not substantively affect the properties of the polymer disclosed herein. For example, a comonomer can be present in an amount of less than about 0.5 wt. %, 0.1 wt. %, or 0.01 wt. % based on the total weight of polymer.

In an embodiment, the PE base polymer is characterized by a density of equal to or greater than about 0.945 g/cc, alternatively greater than about 0.950 g/cc, alternatively greater than about 0.955 g/cc, or alternatively greater than about 0.960 g/cc as determined in accordance with ASTM D 1505.

In an embodiment, the PE base polymer may have any suitable modality. Herein, the "modality" of a polymer resin refers to the form of its molecular weight distribution curve, i.e. the appearance of the graph of the polymer weight fraction as a function of its molecular weight. The polymer weight fraction refers to the weight fraction of molecules of a given size. A polymer having a molecular weight distribution curve showing a single peak may be referred to as a unimodal polymer, a polymer having curve showing two distinct peaks may be referred to as bimodal polymer, a polymer having a curve showing three distinct peaks may be referred to as trimodal polymer, etc. Polymer modality can be determined using any suitable methodology such as those described in the examples sections herein.

The PE compositions disclosed herein may have a variety of properties and parameters described below either singularly or in combination. These properties and parameters may be determined using any suitable methodology.

The molecular weight distribution (MWD) of the PE base polymer may be characterized by the ratio of the weight average molecular weight to the number average molecular weight, which is also referred to as the polydispersity index (PDI) or more simply as polydispersity. The number average molecular weight ($M_n$) is the common average of the molecular weights of the individual polymers calculated by measuring the molecular weight of n polymer molecules, summing the weights, and dividing by n. The weight average molecular weight ($M_w$) of the polymer composition is calculated according to equation 1:

$$M_w = \frac{\Sigma_i N_i M_i^2}{\Sigma_i N_i M_i} \qquad (1)$$

where $N_i$ is the number of molecules at molecular weight $M_i$. All molecular weight averages are expressed in kilogram per mol (kg/mol). Various moments of the MWD include the z-average molecular weight ($M_z$) which is a higher order molecular weight average and the viscosity average molecular weight ($M_v$).

In an embodiment, the PE base polymer has a $M_w$ of from about 80 kg/mol to about 200 kg/mol; alternatively of from about 90 kg/mol to about 175 kg/mol; or alternatively of from about 100 kg/mol to about 150 kg/mol and a MWD of from about 2 to about 20, alternatively from about 2 to about 15, or alternatively from about 2 to about 12.

In an embodiment, a PE base polymer of the type described herein has a melt index, MI, in the range of from about 0.5 grams per 10 minutes (g/10 min) to about 4.0 g/10 min, alternatively from about 0.7 g/10 min to about 3.0 g/10 min, or alternatively from about 0.75 g/10 min to about 2.75 g/10 min. The melt index (MI) refers to the amount of a polymer which can be forced through a melt indexer orifice of 0.0825 inch diameter when subjected to a force of 2.160 kg in ten minutes at 190° C., as determined in accordance with ASTM D 1238.

In an embodiment, a CIB comprises a mixture of a PE base polymer and an additive to improve the MVTR (AIM). In an embodiment, the AIM is a wax. Examples of waxes suitable for use in the present disclosure include without limitation olefin waxes, alpha olefin waxes, oxidized alpha olefin waxes, Fischer-Tropsch waxes, paraffins, montan waxes, and combinations thereof.

In an embodiment, the AIM is an olefin wax, alternatively an alpha-olefin wax or alternatively an oxidized alpha olefin wax. Generally, the olefin wax can comprise, or consist essentially of, any olefin having at least 20 carbon atoms. In an embodiment, the olefin can comprise, or consist essentially of, an internal olefin, an alpha olefin, or any combination thereof; alternatively, an internal olefin; or alternatively, an alpha olefin. In some embodiments, the olefins of the olefin wax (e.g., internal olefin and/or alpha olefin) can comprise, or consist essentially of, linear olefins, branched olefins, or any combination thereof; alternatively, a linear olefin; or alternatively, a branched olefin. In other embodiments, the olefin wax can comprise, or consist essentially of, linear internal olefins; alternatively, linear alpha olefins. In yet other embodiments, the olefin wax can comprise a normal alpha olefin. In an embodiment, the olefin wax can comprise a mixture of one or more olefins selected from the group consisting of linear alpha olefins, linear internal olefins, branched alpha olefins, and branched internal olefins. In some embodiments, the olefin wax (regardless of whether it comprises linear or branched olefins and/or alpha olefin or internal olefins) can comprise, or consist essentially of, hydrocarbon olefins. Additional criteria which can be independently utilized, either singly or in any combination, to describe the olefin wax can include the olefin content, paraffin content, average olefin molecular weight, carbon number composition, alpha olefin content, internal olefin content, linear internal olefin content, vinylidene and olefin content, among other properties disclosed herein. The olefin wax which can be oxidized can be referred to as a feedstock olefin wax.

In an aspect, the olefin wax can comprise greater than or equal to 35 mole percent olefins; alternatively, greater than or equal to 45 mole percent olefins; alternatively, greater than or equal to 50 mole percent olefins; alternatively, greater than or equal to 60 mole percent olefins; alternatively, greater than or equal to 70 mole percent olefins; alternatively, greater than or equal to 75 mole percent olefins; alternatively, greater than or equal to 85 mole percent olefins; alternatively, greater than or equal to 90 mole percent olefins; or alternatively, greater than or equal to 95 mole percent olefins. In an aspect, the olefin wax can comprise greater than or equal to 35 weight percent olefins; alternatively, greater than or equal to 45 weight percent olefins; alternatively, greater than or equal to 50 weight percent olefins; alternatively, greater than or equal to 60 weight percent olefins; alternatively, greater than or equal to 70 weight percent olefins; alternatively, greater than or equal to 75 weight percent olefins; alternatively, greater than or equal to 85 weight percent olefins; alternatively, greater than or equal to 90 weight percent olefins; or alternatively, greater than or equal to 95 weight percent olefins. Generally, the quantity of olefins (in either weight or mole percent) in the olefin wax is based upon the entire amount of olefin wax (weight or number of moles).

In an embodiment, the olefin wax can contain less than 65 mole percent paraffin; alternatively, less than 50 mole percent paraffin; alternatively, less than 35 mole percent paraffin; alternatively, less than 20 mole percent paraffin; alternatively, less than 8 mole percent paraffin; or alternatively, less than 5 mole percent paraffin. In another embodiment, the olefin wax can contain less than 65 weight percent paraffin; alternatively, less than 50 weight percent paraffin; alternatively, less than 35 weight percent paraffin; alternatively, less than 20 weight percent paraffin; alternatively, less than 8 weight percent paraffin; or alternatively, less than 5 weight percent paraffin. Generally, the paraffin content of the olefin wax (in either weight or mole percent) is based upon the entire amount of olefin wax (weight or number of moles).

In an embodiment, the olefin wax can comprise olefins having at least 20 carbon atoms per olefin molecule; alternatively, at least 24 carbon atoms per olefin molecule; alternatively, at least 26 carbon atoms per olefin molecule; alternatively, at least 28 carbon atoms per olefin molecule; or alternatively, at least 30 carbon atoms per olefin molecule. In another embodiment, the olefin wax can comprise olefins having from 20 carbon atoms per olefin molecule to 30 carbon atoms per olefin molecule; alternatively, having from 20 carbon atoms per olefin molecule to 24 carbon atoms per olefin molecule; alternatively, having from 24 carbon atoms per olefin molecule to 28 carbon atoms per olefin molecule; or alternatively, having from 26 to 28 carbon atoms per olefin molecule. In an embodiment, the paraffin which can be present in the olefin wax can have the same carbon number(s) (or carbon number ranges) as recited for the olefins of the olefin wax.

The olefin wax can comprise olefins having various carbon numbers, as described herein. In an embodiment, the olefins of the olefin wax can comprise greater than 30 mole percent olefins having any herein recited number of carbon atoms; alternatively, greater than 45 mole percent olefins having any herein recited number of carbon atoms; alternatively, greater than 50 mole percent olefins having any herein recited number of carbon atoms; alternatively, greater than 60 mole percent olefins having any herein recited number of carbon atoms; alternatively, greater than 70 mole percent olefins having any herein recited number of carbon atoms; alternatively, greater than 75 mole percent olefins having any herein recited number of carbon atoms; alternatively, greater than 80 mole percent olefins having any herein recited number of carbon atoms; alternatively, greater than 85 mole percent olefins having any herein recited number of carbon atoms; alternatively, greater than 90 mole percent olefins having any herein recited number of carbon atoms; or alternatively, greater than 95 mole percent olefins having any herein recited number of carbon atoms. In other embodiments, the olefins of the olefin wax can comprise greater than 50 weight percent olefins having any herein recited number of carbon atoms; alternatively, greater than 60 weight percent olefins having any herein recited number of carbon atoms; alternatively, greater than 70 weight percent olefins having any herein recited number of carbon atoms; alternatively, greater than 80 weight percent olefins having any herein recited number of carbon atoms; alternatively, greater than 85 weight percent olefins having any herein recited number of carbon atoms; alternatively, greater than 90 weight percent olefins having any herein recited number of carbon atoms; or alternatively, greater than 95 weight percent olefins having any herein recited number of carbon atoms. In yet another embodiment, the olefin wax can consist essentially of olefins having any herein recited number of (or range of) carbon atoms.

In a non-limiting embodiment, the olefin wax can comprise greater than or equal to 70 weight percent, 80 weight percent, 85 weight percent, 90 weight percent, or 95 weight percent olefins having greater than or equal to 20 carbon atoms. In some non-limiting embodiments, the olefin wax can comprise greater than or equal to 70 weight percent, 80 weight percent, 85 weight percent, 90 weight percent, or 95 weight percent olefins having from 20 to 30 carbon atoms. In other non-limiting embodiments, the olefin wax can comprise greater than or equal to 70 weight percent, 80 weight percent, 85 weight percent, 90 weight percent, or 95 weight percent olefins having from 20 to 24 carbon atoms. In some other non-limiting embodiments, the olefin wax can comprise greater than or equal to 50 weight percent, 60 weight percent, 70 weight percent, 80 weight percent, or 90 weight percent olefins having from 24 to 28 carbon atoms. In yet other non-limiting embodiments, the olefin wax can comprise greater than or equal to 50 weight percent, 60 weight percent, 70 weight percent, 80 weight percent, or 90 weight percent olefins having from 26 to 28 carbon atoms. In further non-limiting embodiments, the olefin wax can comprise greater than or equal to 70 weight percent, 80 weight percent, 90 weight percent, or 95 weight percent olefins having greater than or equal to 30 carbon atoms. Other combinations of olefin contents and carbon number values or ranges are readily apparent from aspects and embodiments described in the present disclosure.

Independent of the mole percentage or weight percentage of olefins having a particular carbon number (or range of carbon numbers), the olefins of the olefin wax can further comprise a percentage of a particular olefin (e.g., linear olefin, branched olefin, internal olefin, linear internal olefin, branched internal olefin, alpha olefin, linear alpha olefin, branched alpha olefin, normal alpha olefin, or combinations thereof).

In an embodiment, the olefin wax can comprise alpha olefins. In some embodiments, the olefins of the olefin wax can comprise at least 30 mole percent alpha olefins; alternatively, at least 45 mole percent alpha olefins; alternatively, at least 60 mole percent alpha olefins; alternatively, at least 75 mole percent alpha olefins; alternatively, at least 90 mole percent alpha olefins; or alternatively, at least 95 mole percent alpha olefins. In some embodiments, the olefins of the olefin wax can comprise from 50 to 99 mole percent alpha olefins; alternatively, from 55 to 98 mole percent alpha olefins; alternatively, from 60 to 97 mole percent alpha olefins; or alternatively, from 65 to 95 mole percent alpha olefins.

In an embodiment, the olefin wax can comprise linear alpha olefins. In some embodiments, the olefins of the olefin wax can comprise at least 30 mole percent linear alpha olefins; alternatively, at least 45 mole percent linear alpha olefins; alternatively, at least 60 mole percent linear alpha olefins; alternatively, at least 75 mole percent linear alpha olefins; alternatively, at least 90 mole percent linear alpha olefins; or alternatively, at least 95 mole percent linear alpha olefins. In some embodiments, the olefins of the olefin wax can comprise from 50 to 99 mole percent liner alpha olefins; alternatively, from 55 to 98 mole percent alpha olefins; alternatively, from 60 to 97 mole percent linear alpha olefins; or alternatively, from 65 to 95 mole percent linear alpha olefins.

In an embodiment, the olefin wax can comprise normal alpha olefins. In some embodiments, the olefins of the olefin wax can comprise at least 30 mole percent normal alpha olefins; alternatively, at least 45 mole percent normal alpha olefins; alternatively, at least 60 mole percent normal alpha olefins; alternatively, at least 75 mole percent normal alpha olefins; alternatively, at least 90 mole percent normal alpha olefins; or alternatively, at least 95 mole percent normal alpha olefins. In some embodiments, the olefins of the olefin wax can comprise from 50 to 99 mole percent normal alpha olefins; alternatively, from 55 to 98 mole percent normal alpha olefins; alternatively, from 60 to 97 mole percent normal alpha olefins; or alternatively, from 65 to 95 mole percent normal alpha olefins.

In an embodiment, the olefin wax can comprise vinylidenes. In some embodiments, the olefins of the olefin wax can comprise from 2 to 90 mole percent vinylidenes; alternatively, from 4 to 80 mole percent vinylidenes; or alternatively, 6 to 60 mole percent vinylidenes. In other embodiments, the olefins of the olefin wax can comprise from 4 to 20 mole percent vinylidenes; alternatively, from 5 to 18 mole percent vinylidenes; alternatively, from 6 to 15 mole percent vinylidenes; alternatively, from 7 to 25 mole percent vinylidenes; alternatively, from 9 to 20 mole percent vinylidenes; alternatively, from 11 to 17 mole percent vinylidenes; alternatively, from 10 to 30 mole percent vinylidenes; alternatively, from 12 to 18 mole percent vinylidenes; alternatively, from 15 to 25 mole percent vinylidenes; alternatively, from 20 to 65 mole percent vinylidenes; alternatively, from 22 to 60 mole percent vinylidenes; alternatively, from 25 to 55 mole percent vinylidenes; or alternatively, from 25 to 45 mole percent vinylidenes.

Generally, the carbon number of the alpha olefins (general, linear, or normal) and/or vinylidenes present in the olefins of the olefin wax can be any carbon number disclosed herein for the olefins of the olefin wax.

Generally, the olefin wax can be described using any percentage of olefins present in the olefin wax in combination with any percentage of any particular olefin type (or olefin types such that the total of the olefin types do not total over 100 percent). Additionally, other olefin wax properties described herein can be utilized to further describe the olefin wax. In a non-limiting embodiment, the olefin wax can comprise at least 90 weight percent olefins having from 20 to 24 carbon atoms and the olefins of the olefin wax can comprise at least 75 mole percent normal alpha olefins having from 20 to 24 carbon atoms; alternatively, the olefin wax can comprise at least 70 weight percent olefins having from 24 to 28 carbon atoms and the olefins of the olefin wax can comprise at least 45 mole percent normal alpha olefins having from 24 to 28 carbon atoms; alternatively, the olefin wax can comprise at least 90 weight percent olefins having from 26 to 28 carbon atoms and at least 75 mole percent normal alpha olefins having from 26 to 28 carbon atoms; alternatively, the olefin wax can comprise at least 80 weight percent olefins having at least 30 carbon atoms and the olefin of the olefin wax can comprise at least 45 mole percent normal alpha olefins having at least 30 carbon atoms; or alternatively, the olefin wax can comprise at least 85 weight percent olefins having at least 30 carbon atoms and the olefin of the olefin wax can comprise at least 75 mole percent normal alpha olefins having at least 30 carbon atoms. Other combinations of the percentage of olefin present in the olefin wax and the percentage of a particular olefin type are readily apparent from the present disclosure.

In an embodiment, the olefin wax can have a particular average molecular weight. In an embodiment, the olefin wax can have an average molecular weight of at least 210 grams per mole; alternatively, at least 240 grams per mole; alternatively, at least 260 grams per mole; alternatively, at least 330 grams per mole; or alternatively, at least 450 grams per mole. In some embodiments, the olefin wax can have an average molecular weight ranging from 210 grams per mole to 550 grams per mole; alternatively, ranging from 240 grams per mole to 500 grams per mole; or alternatively, ranging from 270 grams per mole to 450 grams per mole. In other embodiments, the olefin wax can have an average molecular weight ranging from 210 grams per mole to 390 grams per mole; alternatively, ranging from 260 grams per mole to 340 grams per mole; alternatively, ranging from 280 grams per mole to 320 grams per mole; or alternatively, ranging from 285 grams per mole to 310 grams per mole. In another embodiment, the olefin wax can have an average molecular weight ranging from 330 grams per mole to 420 grams per mole; alternatively, ranging from 350 grams per mole to 400 grams per mole; or alternatively, ranging from 360 grams per mole to 390 grams per mole. In yet another embodiment, the olefin wax can have an average molecular weight ranging from 440 grams per mole to 550 grams per mole; alternatively, ranging from 460 grams per mole to 530 grams per mole; or alternatively, ranging from 480 grams per mole to 510 grams per mole. In further embodiments, the olefin wax can have an average molecular weight ranging from 480 grams per mole to 700 grams per mole; alternatively, ranging from 500 grams per mole to 640 grams per mole; or alternatively, ranging from 500 grams per mole to 580 grams per mole.

Commercially available olefin waxes commonly contain a number of alpha olefins having at least about 20 carbon atoms per olefin molecule as well as other compounds (such as for example, smaller alpha olefins, smaller normal alpha olefins, internal olefins, vinylidene, or others). For example, Alpha Olefin $C_{20\text{-}24}$ (available from Chevron Phillips Chemical Company LP, The Woodlands, Tex.) can comprise about 35-55 wt % $C_{20}$ olefin, about 25-45 wt % $C_{22}$ olefin, about 10-26 wt % $C_{24}$ olefin, about 3 wt % olefins smaller than $C_{20}$, and about 2 wt % olefins larger than $C_{24}$. Alpha Olefin $C_{20\text{-}24}$ is an exemplary olefin wax within the definition "comprising an olefin having at least 20 carbon atoms per olefin molecule" as used herein. The disclosure is not limited to this or any other particular commercially available olefin wax. Also, an olefin wax consisting essentially of an olefin having 20 carbon atoms per olefin molecule (or another olefin having a particular number of carbon atoms per olefin molecule greater than 20) can be used herein.

Commercially available olefin waxes can further comprise vinylidene or internal olefins, up to as much as about 40-50 wt % of the olefin wax. In one embodiment, and regardless of the characteristics of the normal alpha olefin waxes AlphaPlus® C20-24, AlphaPlus® C24-28, AlphaPlus® C26-28, AlphaPlus® C30+, and AlphaPlus® C30+HA, which are provided for illustrative purposes as exemplary olefin waxes. The disclosure is not limited to these particular olefin waxes.

TABLE 1

| Characteristic | Typical Value (Typical Range) | | | | |
| --- | --- | --- | --- | --- | --- |
|  | AlphaPlus ® C20-24 | AlphaPlus ® C24-28 | AlphaPlus ® C26-28 | AlphaPlus ® C30+ | AlphaPlus ® C30+ HA |
| $\leq C_{18}$ (wt %) | 0.6 | | | | |
| $C_{20}$-$C_{24}$ (wt %) | 98.6 | | | | |
| $\geq C_{26}$ (wt %) | 0.8 | | | | |
| $\leq C_{22}$ (wt %) | | 0.4 | | | |
| $C_{24}$-$C_{28}$ (wt %) | | 70.8 | | | |
| $\geq C_{30}$ (wt %) | | 18.8 | | | |
| $\leq C_{24}$ (wt %) | | | 1.2 | | |
| $C_{26}$-$C_{28}$ (wt %) | | | 96.2 | | |
| $\geq C_{30}$ (wt %) | | | 2.6 | | |
| $\leq C_{28}$ (wt %) | | | | 11.4 | 4.5 |
| $\geq C_{30}$ (wt %) | | | | 88.6 | 95.5 |
| Mole % Alpha Olefins ($^1$H-NMR) | 86 (83-92) | 54 (40-60) | 79 (70-82) | 62 (50-65) | 76 (70-81) |
| Mole % Vinylidenes ($^1$H-NMR) | 8 (6-15) | 30 (25-55) | 16 (11-20) | 30 (25-45) | 18 (15-25) |
| Mole % Internal olefins ($^1$H-NMR) | 3 (2-5) | 18 (10-22) | 3 (2-8) | 10 (5-20) | 5.3 (4-10) |
| Drop melt point, ° F. (ASTM D 127) | 96 | 151 (140-158) | 125 (122-130) | 162 (154-174) | 159 (150-164) |
| Oil content (MEK extraction), wt. % | | 3.7 (3.0-5.1) | 4.6 (3.2-6.0) | 1.9 (1.0-3.0) | 1.5 (1.0-3.0) |
| Needle Penetration @ 77° F., dmm | 150 | 59 (48-70) | 48 (40-60) | 13 (11-17) | 15.5 (12-18) |
| Needle Penetration @ 100° F., dmm | | | | 24 (18-30) | 32 (24-44) |
| Needle Penetration @ 110° F., dmm | | | | 34 (25-50) | 40 (30-56) |
| Flash Point (ASTM D 93) | 362° F. (183° C.) | 425° F. (218° C.) | 417° F. (214° C.) | 485° F. (252° C.) | 432° F. (222° C.) |
| Saybolt Color | 30 | 25 | 30 | 20+ | 20+ |
| Kinematic Viscosity @ 100° C., cSt | 2.0 (1.8-2.2) | 3.5 (3.2-4.0) | 3.4 (3.2-3.6) | 6.8 (5.0-10.0) | 6.7 (5.0-9.0) | number of carbons in the olefin, the olefin wax is a high alpha (HA) alpha olefin wax. By "HA wax" is meant a wax comprising (a) one or more alpha olefins and (b) less than about 20 wt % vinylidene or internal olefins.

In an embodiment, the olefin wax can have a saponification number less than 5 mg KOH per gram ("g") olefin wax, 2.5 mg KOH per g olefin wax, or 1 mg KOH per g olefin wax. In an embodiment, the olefin wax can have an acid number less than 5 mg KOH per g olefin wax, 2.5 mg KOH per g olefin wax, 1 mg KOH per g olefin wax, or 0.5 mg KOH per g olefin wax.

Olefin waxes which can be utilized as the olefin wax can include olefin streams from ethylene oligomerization, cracked heavy waxes (e.g. Fischer-Tropsch waxes), and mixtures of paraffins and olefins, among others. In an embodiment, the olefin wax can be a Fischer-Tropsch wax comprising a mixture of paraffin waxes and olefin waxes which meet the described herein olefin wax features. One source of commercially available Fischer-Tropsch waxes is Sasol, Johannesburg, South Africa.

In some embodiments, the olefin wax can comprise, or consist essentially of, commercially available normal alpha olefin waxes. One source of commercially available alpha olefin waxes is Chevron Phillips Chemical Company LP, The Woodlands, Tex. Table 1 provides physical and chemical In an embodiment, the AIM comprises an oxidized olefin wax. Generally, the oxidized olefin wax can be produced by any suitable methodology such as by contacting an olefin wax with an oxidizing material to produce an oxidized olefin wax. In an embodiment, an oxidized olefin wax can be produced by a method comprising contacting an olefin wax with an oxygen-containing gas to produce an oxidized wax.

In an aspect, the oxidized olefin wax can have desirable properties such as drop melt point, needle penetration, kinematic viscosity, acid number, saponification number, or any combination thereof. In some embodiments, the desirable properties can be described in relation to the same property of the olefin wax from which the oxidized olefin wax was produced. These oxidized olefin wax properties are independently described herein and can be utilized in any combination to describe the oxidized olefin wax.

In general, the absolute value of the needle penetration of the oxidized olefin wax can be influenced by the needle penetration of the olefin wax from which it can be produced. In turn, the needle penetration of the olefin wax can vary widely depending upon the compositional makeup of the olefin wax. Consequently, the needle penetration of the oxidized olefin wax can be described in relation to the needle penetration of the olefin wax from which it can be produced. In an embodiment, the oxidized olefin wax can have a 25° C. needle penetration value less than the 25° C. needle penetration value of the olefin wax from which it was produced. In some embodiments, the oxidized olefin wax can have a needle penetration value at least 5% less than the needle penetration value of the olefin wax; alternatively, at least 10% less than the needle penetration value of the olefin wax; alternatively, at least 20% less than the needle penetration value of the olefin wax; alternatively, at least 30% less than the needle penetration value of the olefin wax; alternatively, at least 40% less than the needle penetration value of the olefin wax; or alternatively, at least 50% less than the needle penetration value of the olefin wax. In another embodiment, the oxidized olefin wax can have a needle penetration value between 400 percent greater than and 75 percent less than the needle penetration value of the olefin wax; alternatively, from 0 percent greater to 400 percent greater than the needle penetration of the olefin wax; alternatively, from 0 percent greater to 300 percent greater than the needle penetration of the olefin wax; alternatively, from 0 percent greater to 200 percent greater than the needle penetration of the olefin wax; or alternatively, from 0 percent greater to 100 percent greater than the needle penetration of the olefin wax composition.

In general, the absolute value of the drop melt point of the oxidized olefin wax is influenced by the drop melt point of the olefin wax from which it is produced. In turn, the drop melt point of the olefin wax can vary widely depending upon the compositional makeup of the olefin wax. Consequently, the drop melt point of the oxidized olefin wax can be appropriately described in relation to the drop melt point of the olefin wax from which it is produced. In an embodiment, the oxidized olefin wax can have a drop melt point within ±20 percent of the drop melt point of the olefin wax from which it was produced; alternatively, within ±15 percent of the drop melt point of the olefin wax from which it was produced; alternatively, within ±10 percent of the drop melt point of the olefin wax from which it was produced; or alternatively, within ±5 percent of the drop melt point of the olefin wax from which it was produced.

In an embodiment, the 100° C. kinematic viscosity of the oxidized olefin wax can be less than 70 cSt. In another embodiment, the 100° C. kinematic viscosity of the oxidized olefin wax can range from 2 cSt to 80 cSt; alternatively, range from 2 cSt to 70 cSt; alternatively, range from 2.5 cSt to 60 cSt; alternatively, range from 3 cSt to 50 cSt; or alternatively, range from 5 cSt to 25 cSt. In other embodiments, the 100° C. kinematic viscosity of the oxidized olefin wax can be described in relation to the 100° C. kinematic viscosity of the olefin wax from which it is produced. In an embodiment, the 100° C. kinematic viscosity of the oxidized olefin wax can have a 100° C. kinematic viscosity up to 10 times the 100° C. kinematic viscosity of the olefin wax from which it is produced; alternatively, up to 8 times the 100° C. kinematic viscosity of the olefin wax from which it is produced; alternatively, up to 6 times the 100° C. kinematic viscosity of the olefin wax from which it is produced; alternatively, up to 5 times the 100° C. kinematic viscosity of the olefin wax from which it is produced; or alternatively, up to 4 times the 100° C. kinematic viscosity of the olefin wax from which it is produced.

In an embodiment, the oxidized olefin wax can have a saponification number greater than 5 mg KOH per g oxidized olefin wax. In another embodiment, the oxidized olefin wax can have a saponification value ranging from 5 mg KOH per g oxidized olefin wax to 500 mg KOH per g oxidized olefin wax; alternatively, ranging from 7 mg KOH per g oxidized olefin wax to 400 mg KOH per g oxidized olefin wax; alternatively, ranging from 9 mg KOH per g oxidized olefin wax to 300 mg KOH per g oxidized olefin wax; alternatively, ranging from 10 mg KOH per g oxidized olefin wax to 200 mg KOH per g oxidized olefin wax.

In an embodiment, the oxidized olefin wax can have an acid number greater than 1 mg KOH per g oxidized olefin wax. In another embodiment, the oxidized olefin wax can have an acid value ranging from 1 mg KOH per g oxidized olefin wax to 200 mg KOH per g oxidized olefin wax; alternatively, ranging from 2 mg KOH per g oxidized olefin wax to 100 mg KOH per g oxidized olefin wax; alternatively, ranging from 3 mg KOH per g oxidized olefin wax to 75 mg KOH per g oxidized olefin wax; alternatively, ranging from 4 mg KOH per g oxidized olefin wax to 50 mg KOH per g oxidized olefin wax.

Generally, the independently described properties of the oxidized olefin wax can be combined in any manner to describe the oxidized olefin wax. In a non-limiting embodiment, the oxidized olefin wax can have an acid number greater than 1 mg KOH per g oxidized olefin wax and a kinematic viscosity less than about 70 cSt at 100° C. In a non-limiting embodiment, the oxidized olefin wax can have a needle penetration value at 25° C. at least 5 percent less than the needle penetration value at 25° C. of the olefin wax and a kinematic viscosity at 100° C. of up to about 500% greater than the kinematic viscosity of the olefin wax.

In an embodiment, the AIM comprises a Montan wax, also known as a lignite wax, which herein refers to a wax that is derived the solvent extraction of lignite. Montan waxes are the bitumens of lignite that were formed from resins, waxes, and fats of plants from the Tertiary geological period. They are composed of esters of so-called montan acids (fatty acids) with long-chain wax alcohols ranging from $C_{20}$-$C_{36}$ fatty acid esters, alternatively $C_{24}$-$C_{34}$ fatty acid esters. In addition to these components, montan wax can also contain additional free fatty acids and free wax alcohols as well as montan resins, ketones, and asphalt-like material. Montan waxes are generally compositions of various fatty acid esters. In an embodiment, a montan wax suitable for use in the present disclosure has an acid value (mg KOH/g) ranging from about 7 to about 14. Montan is insoluble in water, but is soluble in solvents such as carbon tetrachloride, benzene and chloroform. In addition to naturally derived montan wax, alkyl acids and/or alkyl esters which are derived from high molecular weight fatty acids of synthetic or natural sources with chain lengths of greater than about 18 carbons, alternatively from 26 to 46 carbons that function in a manner similar to naturally derived montan wax are also within the scope of the present disclosure and are included within the scope of "montan wax" as that term is used herein. Such alkyl acids are generally described as being of formula R—COOH, where R is an alkyl non-polar group which is lipophilic and can be from 18 to more than 200 carbons. An example of such as material is octacosanoic acid and its corresponding ester which is, for example, a di-ester of that acid with ethylene glycol. The COOH group forms hydrophilic polar salts in the presence of alkali metals such as sodium or potassium in the emulsion. Such alkyl acids are to be adsorbed onto the surface of the wax particles providing stability in the emulsion in the aqueous phase. Other components which may be added include esterified products of the alkyl acids with alcohols or glycols.

In an embodiment, the AIM comprises STRUKTOL MONTAN WAX OP or STRUCKTOL TR 016 both of which are commercially available from Struktol and have generally the properties presented in Table 2:

TABLE 2

| Typical Properties | |
|---|---|
| Acid Value (mg KOH/g) | 7-14 |
| Density (g/cm$^3$) | 1.01 |
| Dropping point (° C.) | 102 |
| Penetrometer value | 1 |
| Solidification Point (° C.) | 76 |
| Viscosity at 120° C. | ca 400 |

In an embodiment, a CIB of the type disclosed herein can be prepared by any suitable methodology. It is contemplated that all the components used to produce the CIB (e.g., a PE base polymer and an AIM) can be contacted in any order suitable to meet any user and/or process-desired need. A methodology for preparation of the CIB can comprise subjecting the contacted components of the CIB to a blending/mixing procedure. The blending/mixing procedure can be carried out using any suitable apparatus, device, or methodology sufficient to provide an adequate distribution of the components of the CIB and produce a material having the properties described herein.

In an embodiment, a CIB comprises a base polymer of the type disclosed herein present in an amount of from about 93 weight percent (wt. %) to about 99.5 wt. %, alternatively from about 94 wt. % to about 99.5 wt. %, or alternatively from about 95 wt. % to about 99.5 wt. % based on the total weight of the CIB and an AIM of the type disclosed herein present in an amount of from about 0.5 wt. % to about 7 wt. %, alternatively from about 0.5 wt. % to about 6 wt. %, or alternatively from about 0.5 wt. % to about 5 wt. % based on the total weight of the CIB.

In an embodiment, the PE base polymer comprises a metallocene-catalyzed PE homopolymer and the AIM comprises an alpha olefin wax where the PE base polymer is present in an amount of from about 94 wt. % to about 99.5 wt. % based on the total weight of the CIB and the alpha olefin wax is present in an amount of from about 0.5 wt. % to about 6 wt. % based on the total weight of the CIB.

In an embodiment, the PE base polymer comprises a metallocene-catalyzed PE homopolymer and the AIM comprises an oxidized alpha olefin wax wherein the PE base polymer is present in an amount of from about 94 wt. % to about 99.5 wt. % and the oxidized alpha olefin wax is present in an amount of from about 0.5 wt. % to about 6 wt. % based on the total weight of the CIB.

In an embodiment, a CIB of the present disclosure can be formed by inclusion of the AIMs during formation of the PE base polymer. For example, the CIB can be formed by contacting AIMs of the type described herein with an ethylene monomer under the conditions described herein for production of the PE base polymer.

In an embodiment, a method of producing a CIB can comprise melt-extrusion of the components of the CIB. For example, the PE base polymer may be rendered soft or "flowable" in order to facilitate the extrusion/blending process. Any suitable technique can be employed to render the polymeric material soft. In an embodiment, the PE base polymer is exposed to elevated temperatures such as a temperature greater than the melting point of the polymer. For example, the temperature may be from about 360° F. to about 400° F., alternatively from about 365° F. to about 390° F., or alternatively from about 370° F. to about 380° F. The softened PE base polymer can then be contacted with the AIM. In an embodiment, the AIM comprises a wax (e.g., an oxidized alpha olefin wax) which can be added to the softened PE base polymer. In an embodiment, addition of the AIM to the softened PE base polymer can occur prior to the extrusion process. Alternatively, addition of the AIM to the softened PE base polymer occurs during the extrusion process. Melt extrusion is described in greater detail in U.S. Pat. No. 6,528,572, incorporated herein by reference in its entirety.

In an embodiment, a method of producing a CIB can comprise dissolution or mixing extrusion of the components of the CIB (e.g., a PE base polymer and an AIM). In such an embodiment, the PE base polymer and AIM (e.g., oxidized olefin wax) can be dispersed in any suitable solvent. In an embodiment, the PE base polymer and AIM can be solubilized in the same vessel using some appropriate quantity of solvent. It is also contemplated that the PE base polymer can be solubilized in a solvent independently of the AIM.

For example, the PE base polymer can be solubilized in a quantity of solvent in a first vessel and the AIM can be solubilized in a quantity of solvent in a second vessel. In some embodiments, the PE base polymer can be utilized as a solution taken from the end of a PE polymerization process, of the type described previously herein, prior to any drying or solvent removal steps. In such embodiments, the PE base polymer used to prepare the CIB can be the water wet cake obtained from the polymerization process. In an embodiment, the AIM can comprise an oxidized olefin wax that has been contacted with a liquid to form a mixture or melted to form a liquid. The mixture subsequently can be homogenized such as by sonication to form a dispersion. In either embodiment, the two solutions (e.g., PE solution and AIM) can then be combined and blended as appropriate (e.g., sonication) to provide a uniform distribution of all components.

Polymer compositions of the type disclosed herein (i.e., CIB) may be formed into articles of manufacture or end-use articles using any suitable technique such as blown and cast film extrusion, (blow molding, injection molding, fiber spinning, thermoforming).

In an embodiment, polymer compositionss of the type described herein are fabricated into a film. The films of this disclosure may be produced by any suitable method and under any suitable condition for the production of films. In an embodiment, the polymers are formed into films through a cast film process. In a cast film process, plastic melt is extruded through a slot-die, producing a flat film collected on a cardboard roll. Crystallization of the polymer continues in the film up to 48 hours after the process.

The films formed from polymer compositions of this disclosure (e.g., CIB) may be of any thickness desired by the user. Alternatively, the polymers this disclosure may be formed into films having a thickness of from about 0.5 mils to about 5 mils, alternatively from about 0.75 mils to about 2.5 mils, alternatively from about 0.8 mils to about 1.8 mils.

In an embodiment, films formed from polymers of this disclosure may display enhanced barrier properties. For example said films may display a reduced moisture vapor transmission rates (MVTR).

In an embodiment, monolayer films produced from polymers of this disclosure having a thickness ranging from about 1.0 mils to about 1.6 mils may be characterized by an MVTR of from about 0.2 g-mil/100 in$^2$ to about 0.6 g-mil/100 in$^2$, alternatively from about 0.25 g-mil/100 in$^2$ to about 0.5 g-mil/100 in$^2$ or alternatively from about 0.25 g-mil/100 in$^2$ to about 0.45 g-mil/100 in$^2$ as measured in accordance with ASTM F 1249. The MVTR measures passage of gaseous H$_2$O through a barrier. The MVTR may also be referred to as the water vapor transmission rate (WVTR). Typically, the MVTR is measured in a special chamber, divided vertically by the substrate/barrier material. A dry atmosphere is in one chamber, and a moist atmosphere is in the other. A 24-hour test is run to see how much moisture passes through the substrate/barrier from the "wet" chamber to the "dry" chamber under conditions which can specify any one of five combinations of temperature and humidity in the "wet" chamber. The lower the transmission rate, the better is the film at blocking moisture.

The films produced from polymers of this disclosure may be used in the formation of any variety of end-use articles. These end-use articles may include without limitation food packaging for contents such as cereals, crackers, cheese, meat, etc., merchandise bags, t-shirt bags, grocery sacks, produce bags, shrink wrap and, other items. Other non-limiting examples of end-use articles include containers, cups, trays, pallets, toys, or a component of another product. In an embodiment, the polymer compositions disclosed herein (i.e., CM) may be formed into films or coatings which can be useful in food packaging.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner. The following testing procedures were used to evaluate the various polymers and compositions.

Melt index (MI, g/10 min) was determined in accordance with ASTM D 1238, 2.16 kg/190° C. Polymer density was determined in grams per cubic centimeter (g/cc) in accordance with ASTM D 1505.

Molecular weight and molecular weight distributions were measured in 1,2,4-trichlorobenzene (TCB). Rheological breadth refers to the breadth of the transition region between Newtonian and power-law type shear rate for a polymer or the frequency dependence of the viscosity of the polymer. The rheological breadth is a function of the relaxation time distribution of a polymer resin, which in turn is a function of the resin molecular structure or architecture. Assuming the Cox-Merz rule, the rheological breadth may be calculated by fitting flow curves generated linear-viscoelastic dynamic oscillatory frequency sweep experiments with a modified Carreau-Yasuda (CY) model which is represented by equation (2):

$$E = E_o[1 + (T_\xi \dot{\gamma})^a]^{\frac{n-1}{a}} \quad (2)$$

where
E=viscosity (Pa·s)
$\dot{\gamma}$=shear rate (1/s)
a=rheological breadth parameter
$T_\xi$=relaxation time (s) [describes the location in time of the transition region]
$E_o$=zero shear viscosity (Pa·s) [defines the Newtonian plateau]
n=power law constant [defines the final slope of the high shear rate region].

To facilitate model fitting, the power law constant n is held at a constant value. Details of the significance and interpretation of the CY model and derived parameters may be found in: C. A. Hieber and H. H. Chiang, *Rheol. Acta*, 28, 321 (1989); C. A. Hieber and H. H. Chiang, *Polym. Eng. Sci.*, 32, 931 (1992); and R. B. Bird, R. C. Armstrong and O. Hasseger, *Dynamics of Polymeric Liquids, Volume 1, Fluid Mechanics*, 2nd Edition, John Wiley & Sons (1987), each of which is incorporated by reference herein in its entirety. See also R. Byron Bird, Robert C. Armstrong, and Ole Hassager, Dynamics of Polymeric Liquids, Volume 1, Fluid Mechanics, (John Wiley & Sons, New York, 1987.

MVTR was measured in accordance with ASTM F 1249 on cast films of about 1 to 1.6 mils and the MVTR is reported for 90% Relative Humidity (RH) at 100° F. (37.8° C.).

Example 1

Figure 2:
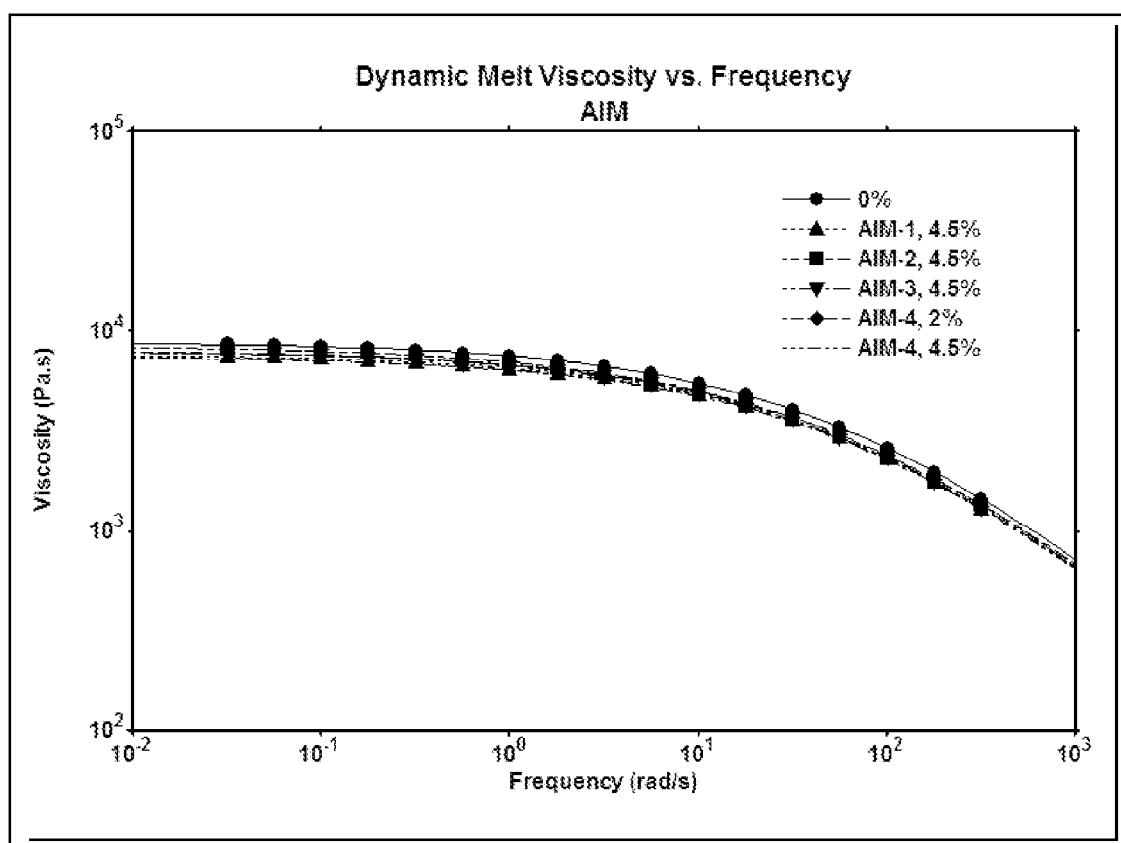
FIG. 2 is a plot of the dynamic melt viscosity as a function of frequency for the samples from example 1.

Metallocene-catalyzed HDPE (m-HDPE) was used as the base PE polymer in the following examples. A CIB of the type disclosed herein was prepared by melt-blending the PE base polymer and the indicated amount of an AIM. AIMs used in this example were STRUKTOL MONTAN WAX OP, STRUCKTOL TR 016, oxy ALPHAPLUS C30 and ALPHAPLUS C30 which were designated AIM-1, AIM-2, AIM-3, and AIM-4, respectively. Oxy ALPHAPLUS C30 is an oxidized olefin wax prepared for Chevron Phillips Chemicals. The SEC and rheological data of the CIB samples, designated samples 1-27, are presented in Table 3. FIGS. 1A, 1B, 1C, and 1D present an overlay of the molecular weight distribution curves for the PE base polymer in the absence and presence of various amounts of the four types of waxes (AIM-1 to AIM-4). FIG. 2 is a plot of the dynamic melt viscosity as a function of frequency for the indicated samples. These data show that the content of the waxes did not affect significantly the properties of the base PE polymer, resulting in a CIB that display a melt strength similar to that of the base PE polymer and allowed for good cast film extrusion and good control of the film gauges.

TABLE 3

| | | | | | Rheology Data # 190° C. | | |
|---|---|---|---|---|---|---|---|
| Sample Number | AIM, wt % | $M_n/1000$, kg/mol | $M_w/1000$, Kg/mol | SEC Data $M_w/M_n$ | Eta_0 Pa-s | Tau, S | Cy-a |
| 1 | 0 | 45 | 140 | 3.1 | 8.8E+03 | 0.0140 | 0.5268 |
| 2 | AIM-1, 2 | 40 | 140 | 3.5 | | | |
| 3 | AIM-1, 3 | 26 | 135 | 5.2 | | | |
| 4 | AIM-1, 3.5 | 30 | 133 | 4.5 | | | |
| 5 | AIM-1, 4 | 24 | 134 | 5.7 | | | |
| 6 | AIM-1, 4.5 | 22 | 137 | 6.2 | 7.7E+3 | 0.0132 | 0.5279 |
| 7 | AIM-1, 5 | 20 | 133 | 6.7 | | | |
| 8 | AIM-1, 6 | 19 | 132 | 6.9 | | | |
| 9 | AIM-2, 2 | 37 | 134 | 3.7 | | | |
| 10 | AIM-2, 3 | 34 | 135 | 4.0 | | | |
| 11 | AIM-2, 3.5 | 32 | 134 | 4.2 | | | |

TABLE 3-continued

| | | | | | Rheology Data # 190° C. | | |
|---|---|---|---|---|---|---|---|
| Sample Number | AIM, wt % | $M_n$/1000, kg/mol | $M_w$/1000, Kg/mol | SEC Data $M_w/M_n$ | Eta_0 Pa-s | Tau, S | Cy-a |
| 12 | AIM-2, 4 | 29 | 135 | 4.6 | | | |
| 13 | AIM-2, 4.5 | 34 | 141 | 4.2 | 8.4E+03 | 0.0130 | 0.4940 |
| 14 | AIM-2, 5 | 29 | 134 | 4.6 | | | |
| 15 | AIM-2, 6 | 28 | 135 | 4.8 | | | |
| 16 | AIM-3, 2 | 28 | 135 | 4.8 | | | |
| 17 | AIM-3, 3 | 23 | 134 | 5.8 | | | |
| 18 | AIM-3, 3.5 | 22 | 134 | 6.2 | | | |
| 19 | AIM-3, 4 | 19 | 132 | 6.9 | | | |
| 20 | AIM-3, 4.5 | 21 | 137 | 6.7 | 7.9E+03 | 0.0134 | 0.5157 |
| 21 | AIM-3, 5 | 19 | 132 | 7.0 | | | |
| 22 | AIM-3, 6 | 15 | 130 | 8.5 | | | |
| 23 | AIM-4, 2 | 19 | 136 | 7.2 | 8.0E+03 | 0.0134 | 0.5250 |
| 24 | AIM-4, 3 | 15 | 133 | 8.6 | | | |
| 25 | AIM-4, 4 | 14 | 133 | 9.8 | | | |
| 26 | AIM-4, 4.5 | 13 | 132 | 10.4 | | | |
| 27 | AIM-4, 5 | 11 | 133 | 12.2 | 7.5E+03 | 0.0130 | 0.5290 |

Figure 3:
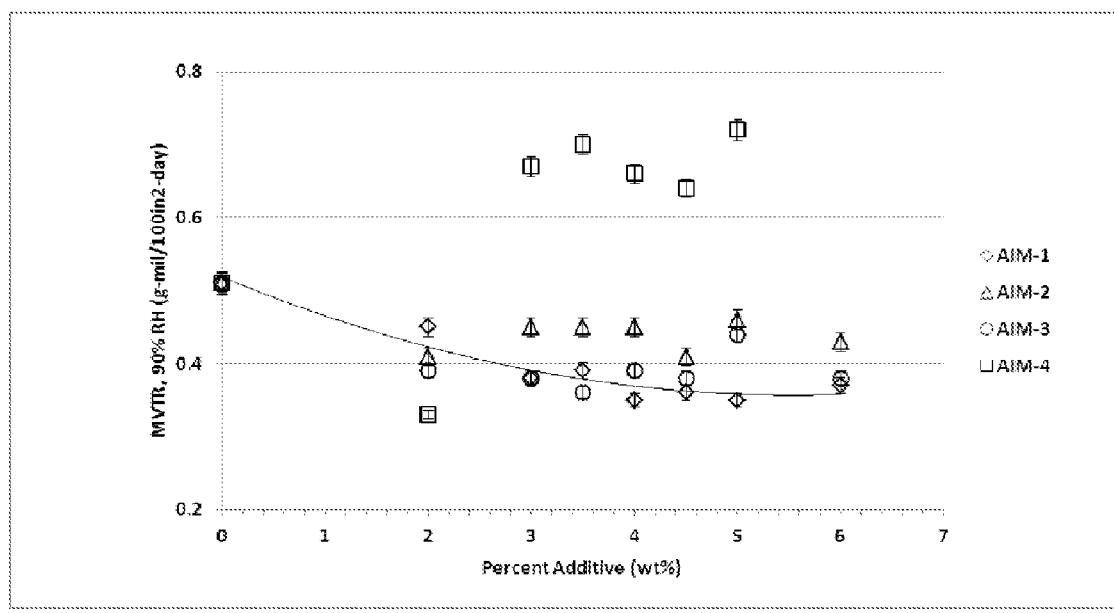
FIG. 3 is a plot of the moisture vapor transmission rate as a function of the percent additive for films formed from the polymer samples of example 1.

The polymer samples were extruded into cast films of 1 to 1.6 mils in thickness at a temperature profile of 375° C. and the MVTR of the films determined according to ASTM F1249. The results of these experiments are presented in Table 4 and plotted in FIG. 3.

TABLE 4

| | Sample Number | | | | | | | |
|---|---|---|---|---|---|---|---|---|
| | 1 | 2 | 3 | 4 | 5 | 6 | 7 | 8 |
| Wt %, AIM-1 | 0 | 2 | 3 | 3.5 | 4 | 4.5 | 5 | 6 |
| Gauge (mil) | 1.2 | 1.1 | 1.2 | 1.2 | 1.4 | 1.2 | 1.3 | 1.2 |
| MVTR, 90% RH, g/100 in²-day | 0.51 | 0.41 | 0.38 | 0.39 | 0.35 | 0.36 | 0.35 | 0.37 |

| | Sample Number | | | | | | | |
|---|---|---|---|---|---|---|---|---|
| | 1 | 9 | 10 | 11 | 12 | 13 | 14 | 15 |
| Wt %, AIM-2 | 0 | 2 | 3 | 3.5 | 4 | 4.5 | 5 | 6 |
| Gauge (mil) | 1.2 | 1.2 | 1.1 | 1.1 | 1.1 | 1.2 | 1.2 | 1.1 |
| MVTR, 90% RH, g/100 in²-day | 0.51 | 0.41 | 0.45 | 0.45 | 0.45 | 0.41 | 0.46 | 0.43 |

| | Sample Number | | | | | | | |
|---|---|---|---|---|---|---|---|---|
| | 1 | 16 | 17 | 18 | 18 | 20 | 21 | 22 |
| Wt %, AIM-3 | 0 | 2 | 3 | 3.5 | 4 | 4.5 | 5 | 6 |
| Gauge (mil) | 1.2 | 1.3 | 1.2 | 1.3 | 1.2 | 1.3 | 1.2 | 1.3 |
| MVTR, 90% RH, g/100 in²-day | 0.51 | 0.39 | 0.38 | 0.36 | 0.39 | 0.38 | 0.44 | 0.38 |

| | Sample Number | | | | | | |
|---|---|---|---|---|---|---|---|
| | 1 | 23 | 24 | 25 | 26 | 27 | 28 |
| Wt %, AIM-4 | 0 | 2 | 3 | 3.5 | 4 | 4.5 | 5 |
| Gauge (mil) | 1.2 | 1.2 | 1.1 | 1.1 | 1.2 | 1.2 | 1.2 |
| MVTR, 90% RH, g/100 in²-day | 0.51 | 0.33 | 0.67 | 0.70 | 0.66 | 0.64 | 0.72 |

The results demonstrate that depending on the type of AIM used, the MVTR performance of the PE base polymer can be improved up to 25% of its original number.

The following enumerated embodiments are provided as non-limiting examples.

A first embodiment which is a composition comprising a polymer and a wax wherein the polymer has a melt index of from about 0.5 g/10 min to about 4 g/10 min, a density of equal to or greater than about 0.945 g/cc which when formed into a film displays a moisture vapor transmission rate of less than about 0.55 g-mil/100 in² in 24 hours as determined in accordance with ASTM F 1249.

A second embodiment which is the composition of the first embodiment wherein the wax comprises olefin waxes, alpha olefin waxes, oxidized olefin waxes, Fischer-Tropsch waxes, paraffins, montan waxes, or combinations thereof.

A third embodiment which is the composition of the second embodiment wherein the olefin wax comprises equal to or greater than 36 mol. % olefins.

A fourth embodiment which is the composition of any of the second through third embodiments wherein the olefin wax comprises less than about 65 mol. % paraffin.

A fifth embodiment which is the composition of any of the second through fourth embodiments wherein the olefin wax has an average molecular weight of at least 210 g/mol.

A sixth embodiment which is the composition of any of the first through fifth embodiments wherein the wax comprises one or more of the following: a) greater than 90 wt % olefins having from 20 to 24 carbon atoms and greater than 75 mol. % alpha olefins having from 20 to 24 carbon atoms; b) greater than 70 wt % olefins having from 24 to 28 carbon atoms and greater than 45 mol. % alpha olefins having from 24 to 28 carbon atoms; c) greater than 90 wt % olefins having from 26 to 28 carbon atoms and greater than 75 mol. % alpha olefins having from 26 to 28 carbon atoms; d) greater than 80 wt % olefins having at least 30 carbon atoms and greater than 45 mol. % alpha olefins having at least 30 carbon atoms; or e) greater than 85 wt % olefins having at least 30 carbon atoms and greater than 75 mol. % alpha olefins at least 30 carbon atoms.

A seventh embodiment which is the composition of any of the second through sixth embodiments wherein the oxidized olefin wax has an acid number greater than 1 mg KOH per g oxidized olefin wax and a kinematic viscosity at 100° C. less than 70 cSt.

An eighth embodiment which is the composition of any of the second through seventh embodiments wherein the oxidized olefin wax has a needle penetration value at 25° C. at least 5 percent less than a needle penetration value at 25° C. of the olefin wax and a kinematic viscosity at 100° C. of up to about 500% greater than the kinematic viscosity of the olefin wax.

A ninth embodiment which is the composition of any of the second through eight embodiments wherein the oxidized olefin wax has a drop melt point greater than the drop melt point of the olefin wax.

A tenth embodiment which is the composition of any of the first through ninth embodiments wherein the polymer is present in an amount of from about 93 wt. % to about 99.5 wt. % and the wax is present in an amount of from about 0.5 wt. % to about 7 wt. %.

An eleventh embodiment which is the composition of any of the first through tenth embodiments wherein the polymer has a weight average molecular weight of from about 80 kg/mol to about 200 kg/mol.

A twelfth embodiment which is the composition of any of the first through eleventh embodiments wherein the polymer has a molecular weight distribution of from about 2 to about 10.

A thirteenth embodiment which is the composition of any of the first through twelfth embodiments wherein the polymer when formed into a film has a haze of less than about 40%.

A fourteenth embodiment which is the composition of any of the first through thirteenth embodiments wherein the polymer comprises polyethylene.

A fifteenth embodiment which is a film formed from the composition of any of the first through thirteenth embodiments.

A sixteenth embodiment which is a film formed from the composition of the fourteenth embodiment.

A seventeenth embodiment which is the film of any of the fifteenth through sixteenth embodiments having a moisture vapor transmission rate of from about 0.25 g-mil/100 in$^2$ in 24 hours as determined in accordance with ASTM F 1249 to about 0.5 g-mil/100 in$^2$ in 24 hours as determined in accordance with ASTM F 1249.

An eighteenth embodiment which is a food packaging container comprising the film of any of the fifteenth through seventeenth embodiments.

A nineteenth embodiment which is a composition comprising a metallocene-catalyzed unimodal polyethylene homopolymer and an oxidized olefin wax wherein the oxidized olefin wax comprises one of more of the following: a) greater than 90 wt % olefins having from 20 to 24 carbon atoms and greater than 75 mol. % alpha olefins having from 20 to 24 carbon atoms; b) greater than 70 wt % olefins having from 24 to 28 carbon atoms and greater than 45 mol. % alpha olefins having from 24 to 28 carbon atoms; c) greater than 90 wt % olefins having from 26 to 28 carbon atoms and greater than 75 mol. % alpha olefins having from 26 to 28 carbon atoms; d) greater than 80 wt % olefins having at least 30 carbon atoms and greater than 45 mol. % alpha olefins having at least 30 carbon atoms; or e) greater than 85 wt % olefins having at least 30 carbon atoms and greater than 75 mol. % alpha olefins at least 30 carbon atoms.

A twentieth embodiment which is a film formed from the composition of the nineteenth embodiment having a moisture vapor transmission rate of from about 0.25 g-mil/100 in$^2$ to about 0.45 g-mil/100 in$^2$ in 24 hours as determined in accordance with ASTM F 1249.

While embodiments of the invention have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference, to the extent that they provide exemplary, procedural or other details supplementary to those set forth herein.

What is claimed is:

1. A composition comprising a polymer and a wax, wherein the wax comprises olefin waxes comprising greater than 50 weight percent of olefins having the same number of carbon atoms, alpha olefin waxes, oxidized olefin waxes, Fischer-Tropsch waxes, paraffins, montan waxes, or combinations thereof; wherein the polymer has a melt index of from about 0.5 g/10 min to about 4 g/10 min, a density of equal to or greater than about 0.945 g/cc, and a moisture vapor transmission rate of less than about 0.55 g-mil/100 in$^2$ in 24 hours as determined in accordance with ASTM F 1249 for a monolayer film at a thickness of from about 1.0 mils to about 1.6 mils.

2. The composition of claim 1 wherein the olefin wax comprises equal to or greater than 36 mol. % olefins.

3. The composition of claim 1 wherein the olefin wax comprises less than about 65 mol. % paraffin.

4. The composition of claim 1 wherein the olefin wax has an average molecular weight of at least 210 g/mol.

5. The composition of claim 1 wherein the wax comprises one or more of the following:
   a) greater than 90 wt % olefins having from 20 to 24 carbon atoms and greater than 75 mol. % alpha olefins having from 20 to 24 carbon atoms;
   b) greater than 70 wt % olefins having from 24 to 28 carbon atoms and greater than 45 mol. % alpha olefins having from 24 to 28 carbon atoms;
   c) greater than 90 wt % olefins having from 26 to 28 carbon atoms and greater than 75 mol. % alpha olefins having from 26 to 28 carbon atoms;
   d) greater than 80 wt % olefins having at least 30 carbon atoms and greater than 45 mol. % alpha olefins having at least 30 carbon atoms; or
   e) greater than 85 wt % olefins having at least 30 carbon atoms and greater than 75 mol. % alpha olefins having at least 30 carbon atoms.

6. The composition of claim 1 wherein the oxidized olefin wax has an acid number greater than 1 mg KOH per g oxidized olefin wax and a kinematic viscosity at 100° C. less than 70 cSt.

7. The composition of claim 1 wherein the oxidized olefin wax has a needle penetration value at 25° C. at least 5 percent less than a needle penetration value at 25° C. of the olefin wax prior to oxidation and a kinematic viscosity at 100° C. of up to about 500% greater than the kinematic viscosity of the olefin wax prior to oxidation.

8. The composition of claim 1 wherein the oxidized olefin wax has a drop melt point greater than the drop melt point of the olefin wax prior to oxidation.

9. The composition of claim 1 wherein the polymer is present in an amount of from about 93 wt. % to about 99.5 wt. % and the wax is present in an amount of from about 0.5 wt. % to about 7 wt. %.

10. The composition of claim 1 wherein the polymer has a weight average molecular weight of from about 80 kg/mol to about 200 kg/mol.

11. The composition of claim 1 wherein the polymer has a molecular weight distribution of from about 2 to about 10.

12. The composition of claim 1 wherein the polymer when formed into a film has a haze of less than about 40%.

13. The composition of claim 1 wherein the polymer comprises polyethylene.

14. A monolayer film formed from the composition of claim 1.

15. A monolayer film formed from the composition of claim 13.

16. The film of claim 14 having a moisture vapor transmission rate of from about 0.25 g-mil/100 in$^2$ in 24 hours as determined in accordance with ASTM F 1249 to about 0.5 g-mil/100 in$^2$ in 24 hours as determined in accordance with ASTM F 1249.

17. A food packaging container comprising the film of claim 14.

18. The composition of claim 1 wherein the olefin wax has an acid value ranging from 7 mg KOH/g to 14 mg KOH/g.

19. The composition of claim 1 wherein the olefin wax comprises greater than 60 mole percent of olefins having the same number of carbon atoms.

* * * * *